(12) United States Patent
Ishii et al.

(10) Patent No.: US 7,795,478 B2
(45) Date of Patent: Sep. 14, 2010

(54) PROCESS FOR PRODUCING OPTICALLY ACTIVE FLUOROBENZYL ALCOHOL

(75) Inventors: Akihiro Ishii, Saitama (JP); Koji Ueda, Fujimino (JP); Manabu Yasumoto, Fujimino (JP)

(73) Assignee: Central Glass Company, Limited, Ube-shi (JP)

( * ) Notice: Subject to any disclaimer, the term of this patent is extended or adjusted under 35 U.S.C. 154(b) by 248 days.

(21) Appl. No.: 12/089,882

(22) PCT Filed: Oct. 4, 2006

(86) PCT No.: PCT/JP2006/319862

§ 371 (c)(1),
(2), (4) Date: Apr. 10, 2008

(87) PCT Pub. No.: WO2007/043407

PCT Pub. Date: Apr. 19, 2007

(65) Prior Publication Data

US 2009/0240087 A1    Sep. 24, 2009

(30) Foreign Application Priority Data

Oct. 14, 2005    (JP) .............................. 2005-299527

(51) Int. Cl.
*C07C 29/09*    (2006.01)

(52) U.S. Cl. ........................ 568/814; 568/810; 568/812

(58) Field of Classification Search ....................... None
See application file for complete search history.

(56) References Cited

U.S. PATENT DOCUMENTS 5,756,862 A    5/1998    Kodama et al.

FOREIGN PATENT DOCUMENTS

JP    9-124527 A    5/1997

OTHER PUBLICATIONS

Allen, A. D. et al., "Solvolysis of 1-Arylethyl Tosylates. Kinetic and Stereochemical Tests for Solvent Participation", J. Am. Chem. Soc., 1985, vol. 107, No. 15, p. 4513-4519.
Pickard, S. T. et al., "Optically Active Amines. 34. Application of the Benzene Chirality Rule to Ring-Substituted Phenylcarbinamines and Carbinols", J. Am. Chem. Soc., 1990, vol. 112, No. 15, p. 5741-5747.
International Search Report dated Nov. 21, 2006 Including English translation of relevant portion (Four (4) pages).
Allan R. Stein et al., "Preparation of Chiral 1-Phenylethanols and Bromides", Canadian Journal of Chemistry, Mar. 29, 1985, pp. 3442-3448, vol. 63, XP-002576471.
European Search Report dated Apr. 15, 2010 (Three (3) pages).

*Primary Examiner*—Brian J Davis
(74) *Attorney, Agent, or Firm*—Crowell & Moring LLP

(57) ABSTRACT

A fluorine-containing benzaldehyde is reacted with an alkyl Grignard reagent to convert it to a magnesium alkoxide of racemic, fluorine-containing, benzyl alcohol, and subsequently the magnesium alkoxide is reacted with phthalic anhydride to obtain a phthalate half ester of racemic, fluorine-containing, benzyl alcohol, and the half ester is optically resolved by optically active 1-phenylethylamine, and then the ester group is hydrolyzed, thereby producing an optically active, fluorine-containing, benzyl alcohol.

3 Claims, No Drawings

PROCESS FOR PRODUCING OPTICALLY ACTIVE FLUOROBENZYL ALCOHOL

TECHNICAL FIELD

The present invention relates to a process for producing an optically active, fluorine-containing, benzyl alcohol, which is an important intermediate of medicines.

BACKGROUND OF THE INVENTION

A process for producing an optically active, fluorine-containing, benzyl alcohol by optically resolving a phthalate half ester of racemic, fluorine-containing, benzyl alcohol by an optically active 1-phenylethylamine and then by hydrolyzing the ester group is publicly known (Non-patent Publication 1 and Non-patent Publication 2).

On the other hand, the following process is disclosed in Non-patent Publication 1 and Non-patent Publication 2 as a process for preparing "a phthalate half ester of racemic, fluorine-containing, benzyl alcohol" which is the starting compound of the process.

That is, in Non-patent Publication 1, a process is taken (the following scheme) in which a fluorine-containing benzaldehyde is reacted with an alkyl Grignard reagent to obtain a magnesium alkoxide of racemic, fluorine-containing, benzyl alcohol, then the magnesium alkoxide is converted to a racemic, fluorine-containing, benzyl alcohol, then the racemic, fluorine-containing, benzyl alcohol is once isolated and purified, and then under a basic condition it is reacted with phthalic anhydride (the following scheme).

Scheme of Non-patent Publication 1 (Preparation Method of [4])

[Chemical Formula 1]

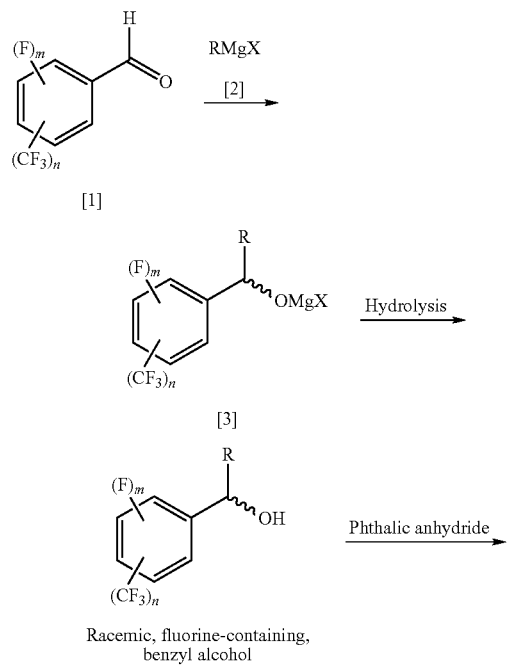

Racemic, fluorine-containing, benzyl alcohol

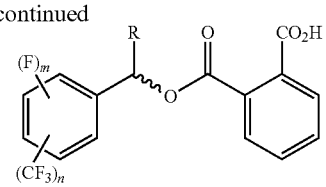

[4]

On the other hand, in Non-patent Publication 2, a process is taken (the following scheme) in which an aliphatic aldehyde is reacted with a fluorine-containing phenyl Grignard reagent, thereby converting it to a magnesium alkoxide of racemic, fluorine-containing, benzyl alcohol, and subsequently it is reacted directly with phthalic anhydride.

Scheme of Non-Patent Publication 2 (Preparation Method of [4])

[Chemical Formula 2]

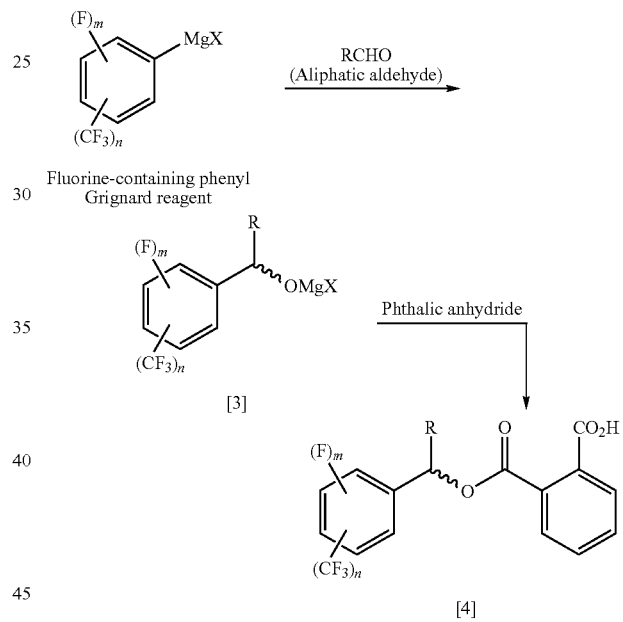

Non-patent Publication 1: Journal of the American Chemical Society (US), 1990, Vol. 112, No. 15, p. 5741-5747

Non-patent Publication 2: Journal of the American Chemical Society (US), 1985, Vol. 107, No. 15, p. 4513-4519

SUMMARY OF THE INVENTION

It is an object of the present invention to provide a process for efficient optical resolution of a fluorine-containing benzyl alcohol, which is an important intermediate of medicines. A process, in which "a phthalate half ester of racemic, fluorine-containing, benzyl alcohol" is optically resolved by an optically active 1-phenylethylamine, and then the ester group is hydrolyzed, is important as a process for providing a wide range of adaptable substrates, since it provides a fluorine-containing benzyl alcohol of high optical purity, irrespective of the substitution position of the fluorine-containing substituent.

However, in the preparation processes mentioned in Non-patent Publication 1 and Non-patent Publication 2, there has been a problem in which the "phthalate half ester of racemic, fluorine-containing, benzyl alcohol" cannot be prepared easily and with good yield. Actually, in Non-patent Publication 1, the synthesis of "racemic, fluorine-containing, benzyl alcohol" and the synthesis of the "phthalate half ester" were conducted separately. Thus, the operation was very complicated in industrial practice [the total yield based on 2-trifluoromethylbenzaldehyde was 61% (RMgX was $CH_3MgBr$)].

In Non-patent Publication 2, the operation is very easy, since the magnesium alkoxide formed in the reaction system is reacted directly with phthalic anhydride without isolation of the racemic, fluorine-containing, benzyl alcohol. However, "a magnesium alkoxide of racemic, fluorine-containing, benzyl alcohol" derived from an aliphatic aldehyde and a fluorine-containing phenyl Grignard reagent did not show a good reactivity to phthalic anhydride. Therefore, it was not possible to obtain the target "phthalate half ester of racemic, fluorine-containing, benzyl alcohol" with good yield [the total yield based on 3-trifluoromethylphenylmagnesium bromide (3-trifluoromethylphenyl bromide) was 43% (the aliphatic aldehyde was $CH_3CHO$)].

Thus, there has been a strong demand for a process capable of preparing a phthalate half ester of racemic, fluorine-containing, benzyl alcohol with ease and good yield in optical resolution of the fluorine-containing, benzyl alcohol.

As a result of an eager examination to solve the above task, the present inventors have found that a phthalate half ester of racemic, fluorine-containing, benzyl alcohol can be prepared very easily and with good yield by reacting a fluorine-containing benzaldehyde with an alkyl Grignard reagent to convert it to a magnesium alkoxide of racemic, fluorine-containing, benzyl alcohol, and by subsequently reacting it with phthalic anhydride (with a total yield of preferably 80% or greater, more preferably 90% or greater, based on the fluorine-containing benzaldehyde).

The reason for good-yield preparation as compared with Non-patent Publication 2 is considered to be the absence of "aliphatic aldehyde" in the reaction, which tends to cause side reactions, such as deprotonation of α-position proton and addition to carbonyl group, by the formed magnesium alkoxide of racemic, fluorine-containing, benzyl alcohol. In Non-patent Publication 2, the racemic, fluorine-containing, benzyl alcohol is actually recovered in a considerable amount (total yield: 28%), and it is considered that the reactivity to phthalic anhydride is greatly lowered through the side reactions.

Furthermore, the present inventors have found that the target, optically active, fluorine-containing, benzyl alcohol can be produced with very high optical and chemical purities by optically resolving the obtained half ester by optically active 1-phenylethylamine and then by hydrolyzing the ester group (the following scheme).

Scheme of the Invention

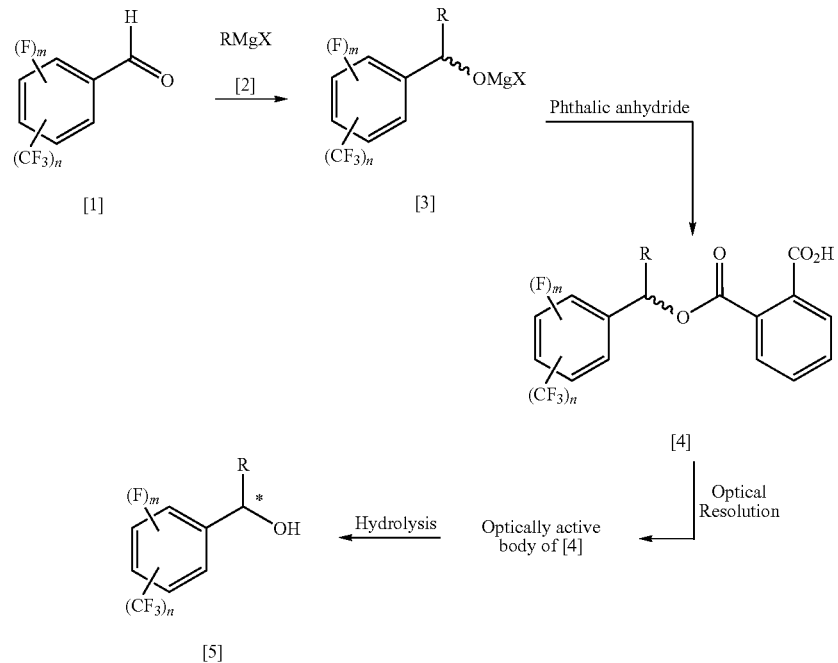

That is, the present invention provides a process (first process) for producing an optically active, fluorine-containing, benzyl alcohol represented by formula [5]

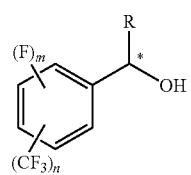

[in the formula, m, n and R are the same as below, and * represents that it is an optically active molecule] by reacting a fluorine-containing benzaldehyde represented by formula [1]

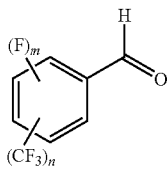

[1]

[in the formula, m represents the number of substituents of fluorine atoms and takes an integer selected from 0, 1, 2, 3, 4 or 5, n represents the number of substituents of trifluoromethyl groups and takes an integer selected from 0, 1, 2 or 3, m and n do not take 0 at the same time, and the total of m and n takes 5 or less] with an alkyl Grignard reagent represented by formula [2]

RMgX    [2]

[in the formula, R represents an alkyl group of a carbon number of 1-6, and X represents a halogen atom selected from chlorine, bromine and iodine], to convert it to a magnesium alkoxide of racemic, fluorine-containing, benzyl alcohol represented by formula [3]

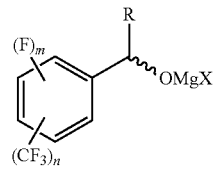

[3]

[in the formula, m, n, R and X are the same as above, and the wavy line represents that it is a racemate], and subsequently by reacting the magnesium alkoxide with phthalic anhydride to obtain a phthalate half ester of racemic, fluorine-containing, benzyl alcohol represented by formula [4]

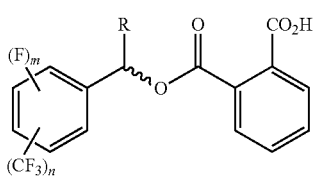

[4]

[in the formula, m, n, R and the wavy line are the same as above], by optically resolving the half ester by optically active 1-phenylethylamine, and then by hydrolyzing the ester group.

The above first process may be a process (second process) for producing an optically active, fluorine-containing, benzyl alcohol represented by formula [10]

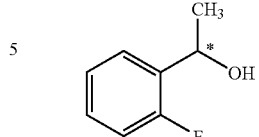

[10]

[in the formula, * represents that it is an optically active body] by reacting a fluorine-containing benzaldehyde represented by formula [6]

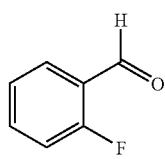

[6]

with an alkyl Grignard reagent represented by formula [7]

CH₃MgCl    [7]

to convert it to a magnesium alkoxide of racemic, fluorine-containing, benzyl alcohol represented by formula [8]

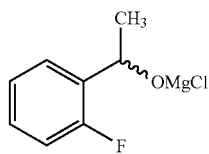

[8]

[in the formula, the wavy line represents that it is a racemate] and subsequently by reacting the magnesium alkoxide with phthalic anhydride to obtain a phthalate half ester of racemic, fluorine-containing, benzyl alcohol represented by formula [9]

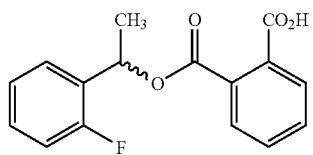

[9]

[in the formula, the wavy line is the same as above], by optically resolving the half ester by optically active 1-phenylethylamine, and then by hydrolyzing the ester group.

The above first process may a process (third process) for producing an optically active, fluorine-containing, benzyl alcohol represented by formula [14]

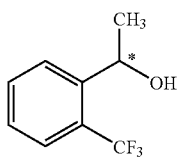

[in the formula, * represents that it is an optically active molecule] by reacting a fluorine-containing benzaldehyde represented by formula [11]

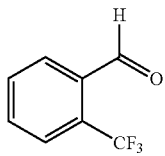

with an alkyl Grignard reagent represented by formula [7]

  [7]

to convert it to a magnesium alkoxide of racemic, fluorine-containing, benzyl alcohol represented by formula [12]

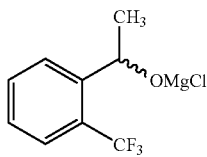

[in the formula, the wavy line represents that it is a racemate] and subsequently by reacting the magnesium alkoxide with phthalic anhydride to obtain a phthalate half ester of racemic, fluorine-containing, benzyl alcohol represented by formula [13]

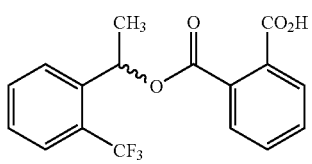

[in the formula, the wavy line is the same as above], by optically resolving the half ester by optically active 1-phenylethylamine, and then by hydrolyzing the ester group.

DETAILED DESCRIPTION

The present invention is characterized in the preparation process of a phthalate half ester of racemic, fluorine-containing benzyl alcohol, and it is possible to prepare the half ester from a fluorine-containing benzaldehyde easily and with a total yield of 80% or greater (more preferably 90% or greater). As a result of this, it is possible to efficiently produce an optically active, fluorine-containing, benzyl alcohol.

Advantageous points of the production process of the present invention as compared with the conventional production techniques are described in the following. As compared with the preparation process written in Non-patent Publication 1, it is not necessary to isolate the racemic, fluorine-containing, benzyl alcohol, and it is possible to continuously conduct the two reactions as a one-pot reaction. Therefore, the operation is very easy in industrial practice. As compared with the preparation process written in Non-patent Publication 2, a magnesium alkoxide of racemic, fluorine-containing, benzyl alcohol, which is derived from a fluorine-containing benzaldehyde and an alkyl Grignard reagent, shows a very good reactivity to phthalic anhydride. Therefore, the target phthalate half ester of racemic, fluorine-containing, benzyl alcohol can be obtained with an extremely good yield.

In the following, the production process (the above first process) of the present invention is explained in detail.

Firstly, the step (step I) of reacting a fluorine-containing benzaldehyde represented by formula [1] with an alkyl Grignard reagent represented by formula [2] is described.

The fluorine atoms or trifluoromethyl groups of the fluorine-containing benzaldehyde represented by formula [1] can take arbitrary substitution positions. Specifically, it is possible to cite 2-fluorobenzaldehyde, 3-fluorobenzaldehyde, 4-fluorobenzaldehyde, 2,4-difluorobenzaldehyde, 2,6-difluorobenzaldehyde, 3,5-difluorobenzaldehyde, 3,4,5-trifluorobenzaldehyde, 2,3,4,5,6-pentafluorobenzaldehyde, 2-trifluoromethylbenzaldehyde, 3-trifluoromethylbenzaldehyde, 4-trifluoromethylbenzaldehyde, 3,5-bis(trifluoromethyl)benzaldehyde, 2-fluoro-3-trifluoromethylbenzaldehyde, 2-fluoro-4-trifluoromethylbenzaldehyde, 2-fluoro-5-trifluoromethylbenzaldehyde, 2-fluoro-6-trifluoromethylbenzaldehyde, 3-fluoro-2-trifluoromethylbenzaldehyde, 3-fluoro-4-trifluoromethylbenzaldehyde, 3-fluoro-5-trifluoromethylbenzaldehyde, 3-fluoro-6-trifluoromethylbenzaldehyde, 4-fluoro-2-trifluoromethylbenzaldehyde, 4-fluoro-3-trifluoromethylbenzaldehyde, and the like.

The optically active, fluorine-containing, benzyl alcohol represented by formula [5], which is the target in the present invention, can also be synthesized by an asymmetric reduction of the corresponding fluorine-containing, phenylalkyl ketone. Effectiveness of the present invention can be obtained to the maximum, in case that the ketone has an extremely high price as compared with the fluorine-containing benzaldehyde, which is the raw material substrate of the present invention and that the reaction between the aldehyde and the alkyl Grignard reagent represented by formula [2] proceeds well without by-production of a reduced body [ArCH$_2$O MgX (Ar represents a fluorine-containing phenyl group, and X represents a halogen atom selected from chlorine, bromine and iodine] and the like.

As a fluorine-containing benzaldehyde satisfying such requirements, it is possible to cite one having a fluorine-containing substituent at ortho-position. Therefore, of the above specific examples, preferable ones are 2-fluorobenzaldehyde, 2,4-difluorobenzaldehyde, 2,6-difluorobenzaldehyde, 2,3,4,5,6-pentafluorobenzaldehyde, 2-trifluoromethylbenzaldehyde, 2-fluoro-3-trifluoromethylbenzaldehyde, 2-fluoro-4-trifluoromethylbenzaldehyde, 2-fluoro-5-trifluoromethylbenzaldehyde, 2-fluoro-6-trifluoromethylbenzaldehyde, 3-fluoro-2-trifluoromethylbenzaldehyde, 3-fluoro-6-trifluoromethylbenzaldehyde, and 4-fluoro-2-trifluoromethylbenzaldehyde. In particular, 2-fluorobenzaldehyde and 2-trifluoromethylbenzaldehyde are more preferable.

As R of the alkyl Grignard reagent represented by formula [2], it is possible to cite methyl, ethyl, propyl, butyl, pentyl and hexyl. One having a carbon number of 3 or greater can take a straight-chain or branched form.

X of the alkyl Grignard reagent represented by formula [2] is selected from chlorine, bromine and iodine. In the present invention, it is particularly important to conduct a good reaction between a magnesium alkoxide of racemic, fluorine-containing, benzyl alcohol represented by formula [3], which is derived from the fluorine-containing benzaldehyde represented by formula [1] and the alkyl Grignard reagent, and phthalic anhydride. This reactivity is influenced by the type of X. Therefore, of the above halogen atoms, chlorine and bromine, with which nucleophilicity of the magnesium alkoxide becomes higher, are preferable, and in particular chlorine is more preferable.

The alkyl Grignard reagent represented by formula [2] can be prepared with reference to publicly known methods, for example, "Jikken Kagaku Koza" 18 Synthesis of Organic Compounds VI—Organic Syntheses Using Metals—p. 59-76, 5th Ed., Edited by The Chemical Society of Japan. Furthermore, various constant concentration ether solutions are on the market, and it is easy to use these.

The amount of the alkyl Grignard reagent represented by formula [2] to be used is not particularly limited. Generally, it suffices to use it in 0.7 moles or greater relative to 1 mol of the fluorine-containing benzaldehyde represented by formula [1]. It is preferably 0.8-1.2 moles, particularly more preferably 0.9-1.1 moles. Although even the use in less than 0.7 moles is not particularly problematic, the fluorine-containing benzaldehyde remains unreacted, and yield of the phthalate half ester of racemic, fluorine-containing, benzyl alcohol represented by formula [4] shows a tendency of decrease. Although even the use in 1.3 moles or greater is not particularly problematic, the alkyl Grignard reagent remains in excess and reacts with phthalic anhydride to consume it. Therefore, it is necessary to use phthalic anhydride in excess. Thus, a range of 0.7-1.2 moles is preferable to economically produce the phthalate half ester of racemic, fluorine-containing, benzyl alcohol with good yield.

The reaction solvent is not particularly limited. Generally, ether-series solvents are preferable. Of them, diethyl ether, tetrahydrofuran, tert-butyl methyl ether, di-i-propyl ether, cyclopentyl methyl ether, and 1,4-dioxane are preferable. In particular, diethyl ether, tetrahydrofuran, tert-butyl methyl ether, and di-i-propyl ether are more preferable. These reaction solvents can be used singly or in combination.

The amount of the reaction solvent used is not particularly limited. Generally, it suffices to use it in 0.1 L (liters) or greater relative to 1 mol of the fluorine-containing benzaldehyde represented by formula [1]. It is preferably 0.15-5 L, particularly more preferably 0.2-3 L. In the case of using a constant-concentration ether solution as the alkyl Grignard reagent represented by formula [2], it is also possible to conduct the reaction only with the part of the solvent contained in the ether solution without newly using a reaction solvent.

The method of reacting the fluorine-containing benzaldehyde represented by formula [1] with the alkyl Grignard reagent represented by formula [2] is not particularly limited. It is preferable that an ether solution of the alkyl Grignard reagent is cooled normally under an inert gas atmosphere, and under stirring the fluorine-containing benzaldehyde (or a solution diluted with the reaction solvent) is gradually added, thereby conducting the reaction with stirring under a further cooled condition. Although even a method of adding the alkyl Grignard reagent to the fluorine-containing benzaldehyde is not particularly problematic, the former method is more preferable to prevent by-production of the above reduced body and the like and to safely handle, in an industrial setting, the alkyl Grignard reagent.

The temperature condition is not particularly limited. Generally, it suffices to conduct it in a range of −100 to +100° C., preferably −80 to +80° C., particularly more preferably −60 to +60° C.

The reaction time is not particularly limited. Generally, it suffices to conduct it in a range of 24 hours or shorter. It depends on a combination of the fluorine-containing benzaldehyde represented by formula [1] and the alkyl Grignard reagent represented by formula [2], the reaction conditions and the like. Therefore, it is preferable to trace the fluorine-containing benzaldehyde remaining unreacted by an analytical means such as gas chromatography, liquid chromatography, NMR or the like and to determine a point at which the aldehyde has almost disappeared, as the end point.

Since the magnesium alkoxide of racemic, fluorine-containing, benzyl alcohol represented by formula [3] is reacted directly with phthalic anhydride in the present invention, a post-treatment of the reaction-terminated liquid is not conducted. It is also possible to stably keep the reaction-terminated liquid for a long time under an inert gas atmosphere.

Next, the step (step II) of reacting the magnesium alkoxide of racemic, fluorine-containing, benzyl alcohol represented by formula [3] with phthalic anhydride is described.

The amount of phthalic anhydride used is not particularly limited. Generally, it suffices to use 0.9 moles or greater, preferably 0.95-1.05 moles, particularly more preferably an equimolar amount, relative to 1 mol of the amount of the alkyl Grignard reagent represented by formula [2] to be used.

The reaction solvent is not particularly limited. Generally, the above ether solvents are preferable.

The amount of the reaction solvent used is not particularly limited. Generally, it is preferable to conduct the reaction only with the part of the solvent contained in the reaction-terminated liquid, in which it has been converted to the racemic, fluorine-containing, benzyl alcohol represented by formula [3], without newly using a reaction solvent.

The method of reacting the magnesium alkoxide of racemic, fluorine-containing, benzyl alcohol represented by formula [3] with phthalic anhydride is not particularly limited. It is preferable that the reaction-terminated liquid, which has been converted to the magnesium alkoxide of racemic, fluorine-containing, benzyl alcohol, is cooled normally under an inert gas atmosphere, and phthalic anhydride (or a solution diluted with the reaction solvent) is gradually added while stirring, thereby conducting the reaction with stirring at room temperature. Although even a method of adding the alkoxide to phthalic anhydride is not particularly problematic, the former method capable of adopting a one-pot reaction, which is industrially easy, is more preferable.

The temperature condition is not particularly limited. Generally, it suffices to conduct it in a range of −100 to +100° C., preferably −80 to +80° C., particularly more preferably −60 to +60° C.

The reaction time is not particularly limited. Generally, it suffices to conduct it in a range of 24 hours or shorter. It depends on the type of the magnesium alkoxide of racemic, fluorine-containing, benzyl alcohol represented by formula [3], the reaction conditions and the like. Therefore, it is preferable to trace the magnesium alkoxide of racemic, fluorine-containing, benzyl alcohol (or the corresponding racemic, fluorine-containing, benzyl alcohol in the reaction check after hydrolysis) remaining unreacted by an analytical means such as gas chromatography, liquid chromatography, NMR or the like and to determine a point at which the alkoxide (or the alcohol) has almost disappeared, as the end point.

The post-treatment is not particularly limited. Generally, it is possible to obtain the target phthalate half ester of racemic, fluorine-containing, benzyl alcohol represented by formula [4] by adding a mineral acid (e.g., hydrochloric acid, hydrobromic acid, sulfuric acid, nitric acid, and the like) to the reaction-terminated liquid, followed by extraction with an organic solvent (e.g., toluene, methylene chloride, ethyl acetate, and the like). Furthermore, according to need, it can be purified to have a higher chemical purity by activated carbon treatment, recrystallization, distillation or column chromatography or the like.

Finally, the step (step III) of optically resolving the phthalate half ester of racemic, fluorine-containing, benzyl alcohol represented by formula [4] and then hydrolyzing the ester group is described.

The present step is publicly known, and it can be conducted with reference to Organic Reactions (US), Vol. II, Chapter 9, p. 376-414, Non-patent Publication 1 and Non-patent Publication 2. Therefore, it is not limited to the following typical production method.

The present step is formed by (step III-A) bringing the phthalate half ester of racemic, fluorine-containing, benzyl alcohol represented by formula [4] into contact with optically active 1-phenylethylamine to obtain a diastereomer salt formed of the phthalate half ester of racemic, fluorine-containing, benzyl alcohol and the optically active 1-phenylethylamine, which is represented by formula [15]

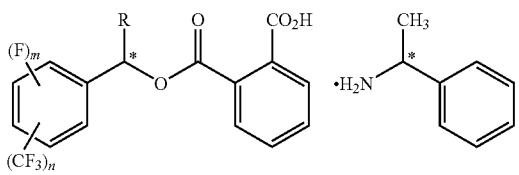

[15]

[in the formula, m represents the number of substituents of fluorine atoms and takes an integer selected from 0, 1, 2, 3, 4 or 5, n represents the number of substituents of trifluoromethyl groups and takes an integer selected from 0, 1, 2 or 3, m and n do not take 0 at the same time, the total of m and n takes 5 or less, R represents an alkyl group of a carbon number of 1-6, each of * independently represents that it is an optically active molecule, and • represents that a salt is formed between the carboxyl group and amino group], (step III-B) conducting a recrystallization purification according to need, and (step III-C) subsequently bringing the diastereomer salt into contact with a strong acid, thereby recovering a phthalate half ester of optically active, fluorine-containing, benzyl alcohol represented by formula [16]

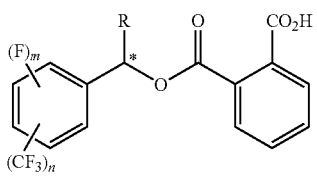

[16]

[in the formula, m, n, R and * are the same as above], and (step III-D) finally, under basic conditions, hydrolyzing the ester group, thereby producing an optically active, fluorine-containing, benzyl alcohol represented by formula [5].

The step III-A is described.

As the method of bringing the phthalate half ester of racemic, fluorine-containing benzyl alcohol represented by formula [4] into contact with optically active 1-phenylethylamine, it is possible to obtain a diastereomer salt, which is represented by formula [15] and is formed of the phthalate half ester of optically active, fluorine-containing, benzyl alcohol and optically active 1-phenylethylamine, by adding the half ester and the amine to a crystal precipitating solvent, by dissolving them through heating at a temperature around boiling point of the solvent, by gradually decreasing the temperature under standing still or stirring to sufficiently precipitate crystals in a range of −30 to +30° C. by spending 1 to 48 hours, and by filtering the precipitated crystals.

As mentioned from the industrial viewpoint, a method is more preferable in which the crystals are precipitated by adding optically active 1-phenylethylamine (or a solution diluted with the crystal precipitating solvent) to the recovering organic layer, with which the phthalate half ester of racemic, fluorine-containing, benzyl alcohol represented by formula [4] has been extracted.

Furthermore, a phthalate half ester of fluorine-containing benzyl alcohol (or a diastereomer salt formed of the half ester and optically active 1-phenylethylamine) having the inverse stereochemistry is contained in excess in the filtrate. Therefore, it is possible to recover a phthalate half ester of optically active, fluorine-containing, benzyl alcohol represented by formula [16], which has the inverse stereochemistry, by conducting an operation similar to that of the step III-C on the concentration residue of the filtrate.

Furthermore, it is also possible to produce an optically active, fluorine-containing, benzyl alcohol represented by formula [5], which has the inverse stereochemistry, by conducting a similar operation in the order of step III-A→step III-B→step III-C→step III-D using an optically active 1-phenylethylamine having the inverse stereochemistry relative to the half ester.

As stereochemistry of the optically active 1-phenylethylamine, it suffices to suitably use R configuration or S configuration in accordance with the target stereochemistry of the optically active, fluorine-containing, benzyl alcohol represented by formula [5].

As optical purity of the optically active 1-phenylethylamine, it suffices to use one having 95% enantiomeric excess (ee) or greater. One having 97% ee or greater is preferable, and particularly one having 99% ee or greater is more preferable.

As the amount of the optically active 1-phenylethylamine used, it suffices to use 0.2 moles or greater, preferably 0.3-3 moles, particularly more preferably 0.4-1.5 moles, relative to 1 mole of the phthalate half ester of racemic, fluorine-containing, benzyl alcohol represented by formula [4].

As the crystal precipitating solvent, it is possible to cite aliphatic hydrocarbon series such as n-pentane, n-hexane, cyclohexane and n-heptane; aromatic hydrocarbon series such as benzene, toluene, ethylbenzene, xylene and mesitylene; halogenated hydrocarbon series such as methylene chloride, chloroform and 1,2-dichloroethane; ether series such as diethyl ether, tetrahydrofuran, tert-butyl methyl ether, di-i-propyl ether, cyclopentyl methyl ether and 1,4-dioxane; ketone series such as acetone, methyl ethyl ketone and methyl i-butyl ketone; ester series such as ethyl acetate and n-butyl acetate; nitrile series such as acetonitrile and propionitrile; alcohol series such as methanol, ethanol, n-propanol, i-propanol and n-butanol; water and the like. Of these, n-hexane, cyclohexane, n-heptane, toluene, xylene, mesitylene, methylene chloride, diethyl ether, tetrahydrofuran, tert-butyl methyl ether, di-i-propyl ether, acetone, ethyl acetate, acetonitrile, methanol, ethanol, and i-propanol are preferable. In particular, n-hexane, n-heptane, toluene, xylene, tetrahydrofuran, ter-butyl methyl ether, acetone, ethyl acetate, acetonitrile, methanol, and i-propanol are more preferable. It is possible to use these crystal-precipitating solvents singly or in combination.

As the amount of the crystal precipitating solvent used, it suffices to use 0.1 L or greater, preferably 0.2-10 L, particularly preferably 0.3-7 L, relative to 1 mol of the phthalate half ester of racemic, fluorine-containing, benzyl alcohol, which is represented by formula [4].

The step III-B is described.

As a method of a recrystallization purification of the diastereomer salt formed of the phthalate half ester of optically active, fluorine-containing, benzyl alcohol and optically active 1-phenylethylamine, which is represented by formula [15], it is possible to purify the diastereomer salt to have a higher optical purity by adding the diastereomer salt, which has been obtained by the step III-A, to a recrystallizing solvent, and, similar to the operation of the step III-A, by dissolving it through heating at a temperature around the boiling point of the recrystallizing solvent, by gradually decreasing the temperature while standing still or stirring to sufficiently precipitate crystals in a range of −30 to +30° C. by spending 1 to 48 hours, and by filtering the precipitated crystals. By repeating this step, it can also be purified to have a further high optical purity. The recrystallization mother liquor can also be recovered in accordance with a usual way and reused.

As the recrystallizing solvent, it is possible to use the crystal precipitating solvent of the step III-A.

The amount of the recrystallizing solvent used is the same as the amount of the crystal precipitating solvent of the step III-A.

In the present step, according to need, it is also possible to more efficiently precipitate crystals by adding seed crystals.

The step III-C is described.

As a method for bringing the diastereomer salt formed of phthalate half ester of optically active, fluorine-containing, benzyl alcohol and optically active 1-phenylethylamine, which is represented by formula [15], into contact with a strong acid, it is possible to recover a phthalate half ester of optically active, fluorine-containing, benzyl alcohol, which is represented by formula [16], by adding the diastereomer salt to an aqueous solution of inorganic acid, followed by a sufficient shaking and an extraction with organic solvent.

As the inorganic acid, it is possible to cite hydrogen chloride, hydrogen bromide, sulfuric acid, nitric acid, and the like. Of these, hydrogen chloride and sulfuric acid are preferable, and particularly hydrogen chloride is more preferable.

As the amount of the inorganic acid used, it suffices to use 0.7 moles or greater, preferably 0.8-7 moles, particularly more preferably 0.9-5 moles, relative to 1 mol of the diastereomer salt formed of the phthalate half ester of optically active, fluorine-containing, benzyl alcohol and the optically active 1-phenylethylamine, which is represented by formula [15].

As the concentration of the inorganic acid aqueous solution, it suffices to use 0.3 normality (N) or greater, preferably 0.4-7N, particularly more preferably 0.5-5 N.

As the organic solvent, it is possible to cite toluene, methylene chloride, ethyl acetate, and the like. Of these, toluene and ethyl acetate are preferable, and particularly toluene is more preferable. It is possible to use these organic solvents singly or in combination.

As the amount of the organic solvent used, it suffices to use 0.1 L or greater, preferably 0.2-7 L, particularly more preferably 0.3-5 L, relative to 1 mol of the diastereomer salt formed of the phthalate half ester of optically active, fluorine-containing, benzyl alcohol and the optically active 1-phenylethylamine, which is represented by formula [15].

As the post-treatment, according to need, it is also possible to subject the recovering organic layer, with which the phthalate half ester of optically active, fluorine-containing, benzyl alcohol represented by formula [16] has been extracted, to water washing, drying, and concentration, to isolate the half ester. As mentioned from the industrial viewpoint, a method is more preferable in which an aqueous solution of an inorganic base of the step III-D is directly added to the recovering organic layer to hydrolyze the ester group. It is also possible to recover the optically active 1-phenylethylamine contained in the acidic water layer side in accordance with a neutralization extraction of usual method to reuse it as the amine of the step III-A.

The step III-D is described.

As a method for hydrolyzing the ester group of the phthalate half ester of optically active, fluorine-containing, benzyl alcohol represented by formula [16] under a basic condition, it is possible to produce the optically active, fluorine-containing, benzyl alcohol represented by formula [5] by reacting the half ester with an aqueous solution of an inorganic base.

As the phthalate half ester of optically active, fluorine-containing, benzyl alcohol represented by formula [16], it is possible to use the isolated product as mentioned above or the recovering organic layer obtained by the extraction. It is also possible to conduct the reaction of the present step in a two-phase system. In such a case, according to need, it is also possible to accelerate the reaction rate by using a phase-transfer catalyst such as a halide of quaternary ammonium or phosphonium. It is, however, possible to obtain good reactivity by employing preferable reaction conditions of the present step, even if the catalyst is not necessarily used.

As the inorganic base, it is possible to cite lithium carbonate, sodium carbonate, potassium carbonate, lithium hydroxide, sodium hydroxide, potassium hydroxide, and the like. Of these, lithium hydroxide, sodium hydroxide, and potassium hydroxide are preferable, and particularly sodium hydroxide and potassium hydroxide are more preferable.

As the amount of the inorganic base used, it suffices to use 1.7 moles or greater, preferably 1.8-15 moles, particularly more preferably 1.9-10 moles, relative to 1 mol of the phthalate half ester of optically active, fluorine-containing, benzyl alcohol represented by formula [16].

As the concentration of an aqueous solution of the inorganic base, it suffices to use 0.5N or greater, preferably 0.7-15N, particularly more preferably 1-10N.

As the reaction solvent, it is possible to cite aromatic hydrocarbon series such as benzene, toluene, ethylbenzene, xylene and mesitylene; halogenated hydrocarbon series such as methylene chloride, chloroform and 1,2-dichloroethane; ether series such as diethyl ether, tetrahydrofuran, ter-butyl methyl ether, di-i-propyl ether, cyclopentyl methyl ether and 1,4-dioxane; nitrile series such as acetonitrile and propionitrile; alcohol series such as methanol, ethanol, n-propanol, i-propanol and n-butanol; water; and the like. Of these, toluene, xylene, mesitylene, methylene chloride, tetrahydrofuran, tert-butyl methyl ether, di-i-propyl ether, acetonitrile, methanol, ethanol and i-propanol are preferable. In particular, toluene, xylene, methylene chloride, tetrahydrofuran, tert-butyl methyl ether, acetonitrile, methanol and i-propanol are more preferable. It is possible to use these solvents singly or in combination. In the case of directly using the recovering organic layer, with which the phthalate half ester of optically active, fluorine-containing, benzyl alcohol represented by formula [16] has been extracted, it is also possible to conduct the reaction only with the part of the solvent contained in the recovering organic layer without newly using the reaction solvent.

As the amount of the reaction solvent used, it suffices to use 0.1 L or greater, preferably 0.2-7 L, particularly more preferably 0.3-5 L, relative to 1 mol of the phthalate half ester of optically active, fluorine-containing, benzyl alcohol represented by formula [16].

As the temperature condition, it suffices to conduct it in a range of −30 to +150° C., preferably −20 to +125° C., particularly more preferably −10 to +100° C.

As the reaction time, it suffices to conduct it in a range of 24 hours or shorter. It depends on a combination of the phthalate half ester of optically active, fluorine-containing, benzyl alcohol and an aqueous solution of the inorganic base, the reaction conditions and the like. Therefore, it is preferable to trace the phthalate half ester of optically active, fluorine-containing, benzyl alcohol remaining unreacted by an analytical means such as gas chromatography, liquid chromatography, NMR or the like and to determine a point at which the half ester has almost disappeared, as the end point.

As the post-treatment, it is possible to produce the target, optically active, fluorine-containing, benzyl alcohol represented by formula [5] by directly separating the reaction-terminated liquid or, according to need, by extraction through adding an organic solvent, such as toluene, methylene chloride or ethyl acetate, or water to concentrate the recovered organic layer. Furthermore, according to need, it can be purified to have a higher chemical purity and optical purity by activated carbon treatment, recrystallization, distillation or column chromatography or the like.

EXAMPLES

In the following, embodiments of the present invention are specifically explained by examples. The present invention is, however, not limited to these examples. The structural formulas and the compound names of examples are expressed as R configuration or S configuration. This means not only an optically pure R configuration or S configuration, but also an optically active condition [for example, R configuration is in 90% ee (R configuration:S configuration=95:5] in which R configuration or S configuration is contained in excess in the course of optical resolution. Optical purity of the moiety of the phthalate half ester of optically active, fluorine-containing, benzyl alcohol of the diastereomer salt formed of the phthalate half ester of optically active, fluorine-containing, benzyl alcohol and the optically active 1-phenylethylamine, which is represented by formula [15], was determined by chiral gas chromatography of the optically active, fluorine-containing, benzyl alcohol obtained by conducting the operation of the step III-D.

Example 1

Under nitrogen atmosphere, 1300 mL (2.60 mol, 1.00 eq) of 2.0M methylmagnesium chloride-tetrahydrofuran solution was cooled, and 322.7 g (2.60 mol, 1.00 eq) of 2-fluorobenzaldehyde was added while adjusting the inside temperature to −20 to +2° C., followed by stirring for 30 minutes under a cooled condition in iced water. Conversion of methylation was 99.9% by determination by gas chromatography. Subsequently, while adjusting the inside temperature to −22 to 0° C., 385.1 g (2.60 mol, 1.00 eq) of phthalic anhydride was added, followed by stirring at room temperature through the night. Conversion of acylation was 99% or greater by determination by $^1$H-NMR. 1300 mL (2.60 mol, 1.00 eq) of 2.0N hydrochloric acid was added to the reaction-terminated liquid, followed by extraction with 650 mL of toluene. The recovered organic layer was washed with 650 mL of brine, dried with anhydrous sodium sulfate, concentrated under reduced pressure, and vacuum dried, thereby obtaining 706.1 g of racemic 1-(2-fluorophenyl)ethyl alcohol phthalate half ester represented by the following formula,

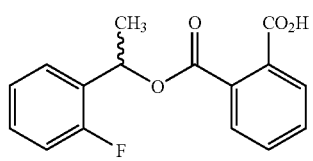

The total yield from 2-fluorobenzaldehyde was 94.2%. 2-fluorobenzyl alcohol phthalate half ester, the reduced body, was not produced as a by-product (less than 1.0% by determination by $^1$H-NMR). $^1$H-NMR and $^{19}$F-NMR spectrums of the obtained racemic 1-(2-fluorophenyl)ethyl alcohol phthalate half ester are shown in the following.

$^1$H-NMR (standard substance: $(CH_3)_4Si$, deuterated solvent: $CDCl_3$), δ ppm: 1.67 (d, 6.4 Hz, 3H), 6.40 (q, 6.4 Hz, 1H), 7.00-7.95 (Ar—H, 8H), and assignment to carboxyl group was not possible.

$^{19}$F-NMR (standard substance: $C_6F_6$, deuterated solvent: $CDCl_3$), δ ppm: 43.56 (m, 1F).

706.1 g (2.45 mol, 1.00 eq) of the half ester and 148.4 g (1.22 mol, 0.50 eq) of (S)-1-phenylethylamine were added to a mixed solution of 5000 mL of i-propanol and 480 mL of methanol, followed by dissolving them by heating at 52° C., gradual cooling to room temperature, filtering the precipitated crystals, and vacuum drying, thereby obtaining 323.8 g of a diastereomer salt of (S)-1-(2-fluorophenyl)ethyl alcohol phthalate half ester(S)-1-phenylethylamine, which is represented by the following formula

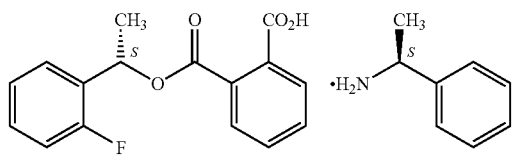

Optical purity of the diastereomer salt was 74.8% ee by determination by chiral gas chromatography. Recovery of the diastereomer salt was 56.4%.

323.8 g of the diastereomer salt was added to a mixed solution of 1650 mL of i-propanol and 920 mL of methanol, followed by dissolving it by heating at 63° C., gradual cooling to 5° C., and filtering the precipitated crystals, thereby obtaining 255.7 g (a product not yet dried) of a recrystallized product of the diastereomer salt of (S)-1-(2-fluorophenyl)ethyl alcohol phthalate half ester(S)-1-phenylethylamine represented by the above formula. Optical purity of the recrystallized product was 99.2% ee by determination by chiral chromatography.

780 mL (1.56 mol, 2.50 eq) of 2.0N hydrochloric acid was added to 255.7 g (set at 0.624 mol, 1.00 eq) of the recrystallized product, followed by extraction with 1000 mL of toluene, thereby obtaining a toluene solution of (S)-1-(2-fluorophenyl)ethyl alcohol phthalate half ester represented by the following formula.

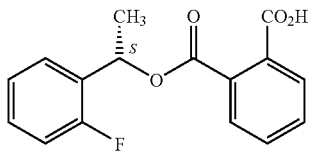

520 mL (3.12 mol, 5.00 eq) of 6.0N sodium hydroxide was added to the toluene solution, followed by stirring at 60° C. for 1 hr. Conversion of the hydrolysis was 100% by determination by $^{19}$F-NMR. The organic layer of the reaction-terminated liquid was separated. The recovered organic layer was washed with 500 mL of 1.0N sodium hydroxide, followed by washing with 500 mL of 10% brine, drying with anhydrous sodium sulfate, concentration under reduced pressure, and vacuum drying, thereby obtaining (S)-1-(2-fluorophenyl)ethyl alcohol represented by the following formula

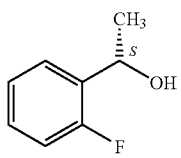

The alcohol was subjected to a fractional distillation (58° C./530 Pa), thereby obtaining 63.5 g of a distillation purified product of (S)-1-(2-fluorophenyl)ethyl alcohol represented by the above formula. Optical purity of the purified product was 99.3% ee by determination by chiral chromatography. Chemical purity of the purified product was 99.9% by determination by gas chromatography. The total yield from the recrystallization purification of the diastereomer salt of (S)-1-(2-fluorophenyl)ethyl alcohol phthalate half ester(S)-1-phenylethylamine was 65.3%. $^1$H-NMR and $^{19}$F-NMR spectrums of the obtained (S)-1-(2-fluorophenyl)ethyl alcohol are shown in the following.

$^1$H-NMR (standard substance: $(CH_3)_4Si$, deuterated solvent: $CDCl_3$), δ ppm: 1.53 (d, 6.8 Hz, 3H), 1.80 (br, 1H), 5.21 (q, 6.8 Hz, 1H), 6.95-7.55 (Ar—H, 4H).

$^{19}$F-NMR (standard substance: $C_6F_6$, deuterated solvent: $CDCl_3$), δ ppm: 41.67 (m, 1F).

Example 2

Under nitrogen atmosphere, 500 mL (1.00 mol, 1.00 eq) of 2.0M methylmagnesium chloride-tetrahydrofuran solution was cooled, and 174.1 g (1.00 mol, 1.00 eq) of 2-trifluoromethylbenzaldehyde was added while adjusting the inside temperature to 4 to 21° C., followed by stirring for 15 minutes under a cooled condition in iced water. Conversion of methylation was 99.9% or greater by determination by gas chromatography. Subsequently, while adjusting the inside temperature to 9 to 37° C., 148.1 g (1.00 mol, 1.00 eq) of phthalic anhydride was added, followed by stirring at room temperature through the night. Conversion of acylation was 99% or greater by determination by $^1$H-NMR. 500 mL (1.00 mol, 1.00 eq) of 2.0N hydrochloric acid was added to the reaction-terminated liquid, followed by extraction with 250 mL of toluene. The recovered organic layer was washed with 250 mL of brine, thereby obtaining 952 g of a toluene solution (containing tetrahydrofuran, too) of racemic 1-(2-trifluoromethylphenyl)ethyl alcohol phthalate half ester represented by the following formula,

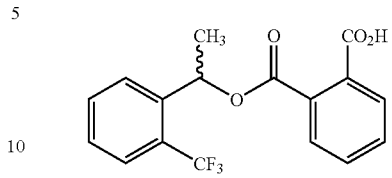

2-trifluoromethylbenzyl alcohol phthalate half ester, the reduced body, was not produced as a by-product (less than 1.0% by determination by $^1$H-NMR).

Under room temperature, while adjusting the inside temperature to 25 to 34° C., a n-heptane solution (the amount of n-heptane used: 500 mL) of (S)-1-phenylethylamine in 60.6 g (0.50 mol, 0.50 eq) was added to 952 g (set at 1.00 mol, 1.00 eq) of the toluene solution, followed by filtering the precipitated crystals, washing with 200 mL of n-heptane, and vacuum drying, thereby obtaining 170.0 g of a diastereomer salt of (S)-1-(2-trifluoromethylphenyl)ethyl alcohol phthalate half ester(S)-1-phenylethylamine, which is represented by the following formula

[Chemical Formula 26]

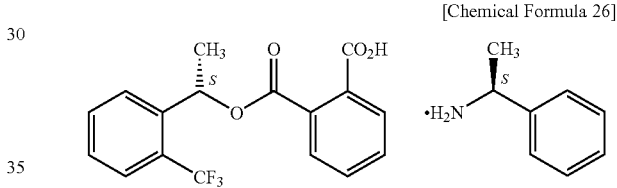

Optical purity of the diastereomer salt was 90.6% ee by determination by chiral gas chromatography. The total yield from 2-trifluoromethylbenzaldehyde was 70.5%.

170.0 g of the diastereomer salt was added to 510 mL of methanol, followed by dissolving it by heating at 60° C., gradual cooling to 5° C., filtering the precipitated crystals, and vacuum drying, thereby obtaining 99.4 g of a recrystallized product of the diastereomer salt of (S)-1-(2-trifluoromethylphenyl)ethyl alcohol phthalate half ester(S)-1-phenylethylamine represented by the above formula. Optical purity of the recrystallized product was 98.9% ee by determination by chiral chromatography. Recovery of the recrystallized product was 61.0%. $^1$H-NMR and $^{19}$F-NMR spectrums of the obtained diastereomer salt of (S)-1-(2-trifluoromethylphenyl)ethyl alcohol phthalate half ester(S)-1-phenylethylamine are shown in the following.

$^1$H-NMR (standard substance: $(CH_3)_4Si$, deuterated solvent: $CDCl_3$), δ ppm: 1.51 (d, 6.8 Hz, 3H), 1.61 (d, 6.8 Hz, 3H), 3.68 (br, 3H), 4.26 (q, 6.8 Hz, 1H), 6.37 (q, 6.8 Hz, 1H), 7.24-7.82 (Ar—H, 13H).

$^{19}$F-NMR (standard substance: $C_6F_6$, deuterated solvent: $CDCl_3$), δ ppm: 103.20 (S, 3F).

185 mL (0.370 mol, 2.00 eq) of 2.0N hydrochloric acid was added to 85.0 g (0.185 mol, 1.00 eq) of the recrystallized product, followed by extraction with 185 mL of toluene. The recovered organic layer was washed with 100 mL of water, thereby obtaining a toluene solution of (S)-1-(2-trifluoromethylphenyl)ethyl alcohol phthalate half ester represented by the following formula.

[Chemical Formula 27]

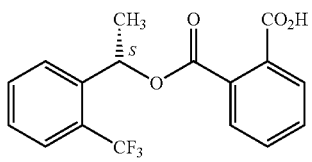

150 mL (0.555 mol, 3.00 eq) of 3.7N potassium hydroxide was added to the toluene solution, followed by stirring at 50° C. for 1 hour and 30 minutes. Conversion of the hydrolysis was 100% by determination by $^{19}$F-NMR. The organic layer of the reaction-terminated liquid was separated, followed by concentration under reduced pressure and vacuum drying, thereby obtaining 34.3 g of (S)-1-(2-trifluoromethylphenyl)ethyl alcohol represented by the following formula

[Chemical Formula 28]

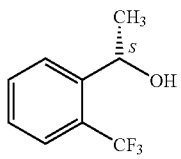

The alcohol was subjected to a fractional distillation (84° C./1330 Pa), thereby obtaining 31.5 g of a distillation purified product of (S)-1-(2-trifluoromethylphenyl)ethyl alcohol represented by the above formula. Optical purity of the purified product was 99.0% ee by determination by chiral chromatography. Chemical purity of the purified product was 99.9% by determination by gas chromatography. The total yield from the recrystallized product of the diastereomer salt of (S)-1-(2-trifluoromethylphenyl)ethyl alcohol phthalate half ester (S)-1-phenylethylamine was 89.6%. $^1$H-NMR and $^{19}$F-NMR spectrums of the obtained (S)-1-(2-trifluoromethylphenyl)ethyl alcohol are shown in the following.

$^1$H-NMR (standard substance: $(CH_3)_4Si$, deuterated solvent: $CDCl_3$), δ ppm: 1.49 (d, 6.4 Hz, 3H), 1.99 (br, 1H), 5.33 (q, 6.4 Hz, 1H), 7.35-7.84 (Ar—H, 4H).

$^{19}$F-NMR (standard substance: $C_6F_6$, deuterated solvent: $CDCl_3$), δ ppm: 103.43 (s, 3F).

The invention claimed is:

1. A process for producing an optically active, fluorine-containing, benzyl alcohol represented by formula [5]

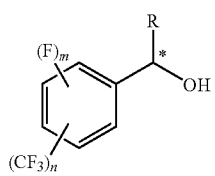

[5]

wherein m is 0, 1, 2, 3, 4 or 5 and represents the number of fluorine atom substituents, n is 0, 1, 2 or 3 and represents the number of trifluoromethyl group substituents, m and n are not both 0 and the total of m and n is 5 or less, R represents an alkyl group with 1-6 carbon atoms, and

* represents that the benzyl alcohol is an optically active molecule, comprising the steps of:

(a) reacting a fluorine-containing benzaldehyde represented by formula [1]

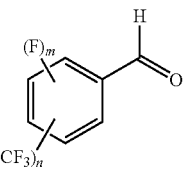

[1]

wherein m and n are defined as above, with an alkyl Grignard reagent represented by formula [2]

RMgX [2]

wherein R is defined as above, and X represents a halogen atom selected from chlorine, bromine and iodine], to convert the benzaldehyde to a magnesium alkoxide of racemic, fluorine-containing, benzyl alcohol represented by formula [3]

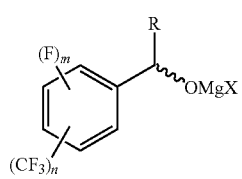

[3]

wherein m, n, R and X are the same as above, and the wavy line represents that it the magnesium alkoxide is a racemate;

(b) reacting the magnesium alkoxide with phthalic anhydride to obtain a phthalate half ester of racemic, fluorine-containing, benzyl alcohol represented by formula [4]

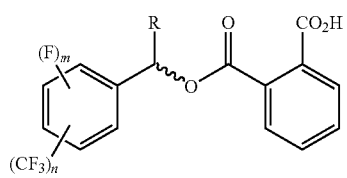

[4]

wherein m, n, R and the wavy line are the same as above;

(c) optically resolving the half ester by optically active 1-phenylethylamine, and (d) hydrolyzing the ester group of the half ester obtained in step (c), thereby obtaining the optically active fluorine-containing benzyl alcohol.

2. A process for producing an optically active, fluorine-containing, benzyl alcohol represented by formula [10]

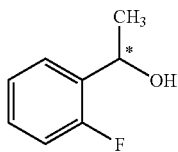
[10]

wherein * represents that the benzyl alcohol is an optically active molecule, comprising the steps of;
(a) reacting a fluorine-containing benzaldehyde represented by formula [6]

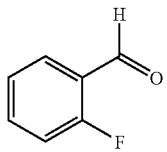
[6]

with an alkyl Grignard reagent represented by formula [7]

CH₃MgCl  [7]

to convert the benzaldehyde to a magnesium alkoxide of racemic, fluorine-containing, benzyl alcohol represented by formula [8]

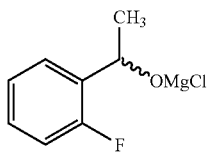
[8]

wherein the wavy line represents that it the magnesium alkoxide is a racemate;
(b) reacting the magnesium alkoxide with phthalic anhydride to obtain a phthalate half ester of racemic, fluorine-containing, benzyl alcohol represented by formula [9]

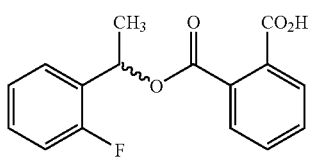
[9]

wherein the wavy line is the same as above;
(c) optically resolving the half ester by optically active 1-phenylethylamine, and
(d) hydrolyzing the ester group of the half ester obtained in step (c), thereby obtaining the optically active, fluorine-containing benzyl alcohol.

3. A process for producing an optically active, fluorine-containing, benzyl alcohol represented by formula [14]

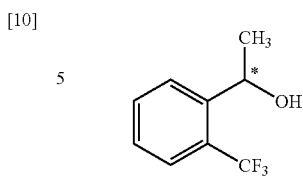
[14]

wherein * represents that it the benzyl alcohol is an optically active molecule, comprising the steps of:
(a) reacting a fluorine-containing benzaldehyde represented by formula [11]

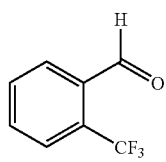
[11]

with an alkyl Grignard reagent represented by formula [7]

CH₃MgCl  [7]

to convert the benzaldehyde to a magnesium alkoxide of racemic, fluorine-containing, benzyl alcohol represented by formula [12]

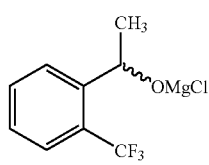
[12]

wherein the wavy line represents that the magnesium alkoxide is a racemate;
(b) reacting the magnesium alkoxide with phthalic anhydride to obtain a phthalate half ester of racemic, fluorine-containing, benzyl alcohol represented by formula [13]

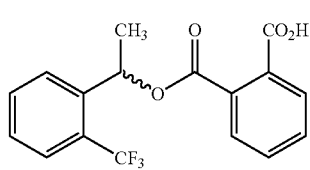
[13]

wherein the wavy line is the same as above;
(c) resolving the half ester by optically active 1-phenylethylamine, and
(d) hydrolyzing the ester group of the half ester obtained in step (c), thereby obtaining the optically active fluorine-containing benzyl alcohol.

* * * * *